United States Patent [19]

Feinstein

[11] Patent Number: 4,572,203
[45] Date of Patent: Feb. 25, 1986

[54] CONTACT AGENTS FOR ULTRASONIC IMAGING

[76] Inventor: Steven B. Feinstein, 295 Hasting Ave., Highland Park, Ill. 60035

[21] Appl. No.: 461,664

[22] Filed: Jan. 27, 1983

[51] Int. Cl.$^4$ ............................................. A61B 10/00
[52] U.S. Cl. ..................................................... 128/661
[58] Field of Search ................................ 128/660–663; 424/1, 4; 73/861.25, 861.41

[56] References Cited

U.S. PATENT DOCUMENTS

| | | | |
|---|---|---|---|
| 4,122,713 | 10/1978 | Stasz et al. ........................... | 128/663 |
| 4,247,406 | 1/1981 | Widder et al. ....................... | 424/1 X |
| 4,265,251 | 5/1981 | Tickner .................................. | 128/662 |
| 4,276,885 | 7/1981 | Tickner et al. | |
| 4,316,391 | 2/1982 | Tickner et al. | |
| 4,466,442 | 8/1984 | Hilmann et al. .................. | 128/660 X |

OTHER PUBLICATIONS

Wells PNT, *Ultrasonics in Clinical Diagnosis*, NY, 1977, pp. 114, 223.
Mansfield P., *NMR Imaging in Biomedicine*, Academic Press, 1982, pp. 233, 234.
Ophir et al., "US Backscatter from Contrast Producing Collagen Microspheres", US Imag 2 (1980) pp. 67–77.
Tickner et al., "Instr for the Non Invasive Assessment of Pulmonary Hypertension", Adv in Bioeng, ASME Sanfran, Dec. 10–15, 1978.
Carroll et al., "Microbubbles as Ultrasonic Contrast Agents", Abstract, 27th Ann Meeting Univ Rochester, May 6–10, 1979.
Rasor et al., "Visualization of Myocardial Perfusion in Intraaortic Injection of Ultrasonic Contrast Agents", 31st Ann Scientific Session, Amer. College of Cardiology, Apr. 25–29, 1982, Atlanta, Ga.
Bommer et al., "Quantitative Regional Myocardial Perfusion Scanning with Contrast Echocardiography.
Armstrong et al, "Contrast Echocardiography for the Detection of Myocardial Perfusion Abnormalities", Abs Circ vol. 64, Supp IV-204, 10/1981.
Yasui et al., "Estimation of Intramyocardial Blood Flow Distr w/ Contrast Echomyocardiography", Abs Circ vol. 66, Supp. 11–28, 10/1982.
Bommer et al., "Developement of a New Echocardiographic Contrast Agent Capable of Pulmonary Trans and Left Heart Opacification Following Peripheral Venous Injections", Abs, 53rd Scientific Sess, Nov. 17–20, 1980.

Primary Examiner—Kyle L. Howell
Assistant Examiner—Francis J. Jaworski
Attorney, Agent, or Firm—Blakely, Sokoloff, Taylor & Zafman

[57] ABSTRACT

A method of ultrasonic imaging for use in medical procedures is disclosed. The method comprises injecting specifically defined microparticles or sonicated microbubbles into an animal or human to thereby alter the acoustic properties of an area to be imaged, and then ultrasonically scanning the area so as to obtain an image.

19 Claims, 5 Drawing Figures

CONTACT AGENTS FOR ULTRASONIC IMAGING

BACKGROUND OF THE INVENTION

1. Field of the Invention

This invention relates to the field of ultrasonic imaging techniques, and more specifically, to a medical procedure which utilizes these techniques as a diagnostic tool.

2. Description of the Prior Art

Various technologies exist in which parts of an animal or human body may be imaged so as to aid in diagnosis and therapy. Some of these existing techniques are described in this section.

One of the most well known imaging techniques involves the use of X-rays to visualize skeletal and other internal structures within animals and humans. There are, however, a number of problems associated with the use of X-rays. First, some areas of the body may not be X-rayed safely. In addition, X-rays are dangerous if the amount of exposure is excessive; further, all X-ray radiation absorbed over a lifetime is cumulative. Finally, while X-rays may produce images of the skeletal and other internal structures, X-rays have proved to be relatively unsatisfactory for detailed viewing of certain organ systems and blood vessels.

Another widely used technique is angiography, whereby a radio-opaque dye is injected into an artery. Because the dye highlights the arteries through which it flows, an X-ray may be used to obtain an image of major, large arteries and their significant branches. However, angiography does not permit visualization of under-perfused, ischemic areas of tissue or heart muscle, or the microcirculation. In addition, certain angiographic observations are based upon measurements which may vary depending upon the apparatus used, the placement and angle of lenses, operator skill and similar factors. Moreover, angiography is invasive in that it requires the placement of a catheter into arteries as opposed to veins. Besides requiring hospitalization, angiography may be dangerous.

Another technique, often referred to as radio-nuclide imaging, involves the injection of radioactive substances, such as thallium, into the blood stream. This technique does not require invasion of the arteries as does angiography, but it does require the use of very expensive and sophisticated machinery. Further, radio-nuclide imaging produces images of only a limited number of views of the heart, and those images may not be of exceptional clarity. Finally, this type of radiation is cumulative over a lifetime and may be dangerous.

Recently, there have been advances in techniques for ultrasonically imaging various parts of the body; these techniques when applied to the heart in particular are known as "echocardiography." An ultrasonic scanner is used to generate and receive sound waves. The ultrasonic scanner is placed on the body surface overlying the area to be imaged. The sound waves generated by the scanner are directed toward the area to be imaged. The scanner then detects sound waves reflected from the underlying area and translates that data into images.

While such ultrasonic scanners are known in the art, a brief review will be set forth in order to more fully explain the present invention. When ultrasonic energy is transmitted through a substance, the acoustic properties of the substance will depend upon the velocity of the transmissions and the density of the substance. Changes in the substance's acoustic properties (or acoustic impedence) will be most prominent at the interface of different substances (i.e., solids, liquids and gases). As a consequence, when ultrasonic energy is directed through various media, the changes in acoustic properties will change the reflection characteristics, resulting in a more intense sound reflection signal received by the ultra-sonic scanner.

Early ultrasonic imaging techniques such as echocardiograms suffered from a lack of clarity. As a result, extensive efforts were undertaken to improve the ultrasonic scanners and related equipment. In addition, beginning in 1968, "contrast" agents were injected into the blood stream in an effort to obtain clearer or "enhanced" ultrasonic images. The prior art contrast agents were liquids containing microbubbles of gas, which sometimes were encapsulated with gelatin or saccharine and sometimes were produced by mechanically agitating, i.e. hand-shaking, mixtures of various liquids. Other prior art contrast agents are disclosed in an article by J. Ophir, et al. entitled "Ultrasonic Backscatter from Contrast Produced by Collagen Microspheres" in Ultrasonic Imaging by Academic Press, Inc. 1980.

The contrast agents themselves are intense sound wave reflectors because of the acoustic differences between the liquid and the gas microbubbles dissolved therein; thus, when the contrast agents are injected into and perfuse the microvasculature of tissue, clearer images of such tissue may be produced. However, notwithstanding the use of such contrast agents, the image produced, for example of the myocardial tissue, is of relatively poor quality, is highly variable and is not quantifiable due to the variable size and persistence associated with prior art microbubbles. Further, the problems of air embolism toxicity have not yet been investigated.

SUMMARY OF THE INVENTION

One embodiment of the present invention is directed to an improvement associated with such prior art contrast agents by which smaller and more uniform microbubbles are produced. A second embodiment is directed to the novel use of specifically defined metal-containing solid or semi-solid contrast agents.

The contrast agents of the present invention are (1) echogenic (i.e., capable of reflecting sound waves), (2) small enough to pass through capillaries so as to perfuse tissue previously inaccessible to the prior art contrast agents injected into a peripheral venous site, thereby producing enhanced images of such tissue and organs and permitting differentiation between well-perfused and poorly-perfused tissue, and (3) quantifiably reproducible. In addition, the metal-containing solid or semi-solid contrast agents of the present invention are free of the potential air embolism toxicity risks associated with the introduction of gaseous bubbles into the human or animal system. It is not believed that such particulate matter has ever been used as a contrast agent in medical procedures.

The method of the present invention (1) permits the imaging of organ systems which could not be imaged using prior art ultrasonic techniques, and (2) permits clearer, more detailed imaging of certain areas which were viewable using such prior art techniques.

In the first embodiment of the present invention, a viscous solution (e.g., 70% Dextrose, 50% Dextrose, 70% Sorbitol, Renografin-76, mixtures of these agents, and the like) is subjected to high frequency (5,000 to 30,000 Hz) ultrasonic energy. As a result, microbubbles having a diameter of approximately 6 to 20 microns are produced. For ease of reference such microbubbles will be referred to herein as "sonicated" microbubbles. As described in greater detail hereinbelow, such sonicated microbubbles have been found to be improved contrast agents.

The second embodiment of the present invention is directed to selected metal-containing microparticles used as contrast agents to reflect intense patterns of sound waves.

The contrast agents of the present invention are detected by conventional ultrasonic scanning equipment and translated into images in the manner described above. The use of the microparticles is especially advantageous in that it obviates the need to introduce gaseous bubbles as contrast agents in the human or animal system, and thus eliminates the air embolism toxicity risks inherent in that procedure. Depending upon whether the microparticles are to be used exclusively in animal research or for diagnostic and therapeutic purposes, the potential biocompatability of the particular type of microparticle is a significant consideration.

The metal-containing microparticles of the present invention are echogenic (i.e., capable of reflecting sound waves), being composed of material having acoustic properties which are significantly different from those of blood or tissue. Their size is small enough to permit their passage through capillaries, if necessary, without being filtered out prior to reaching the area to be imaged (e.g., where a peripheral venous injection site is used); thus, they will be capable of perfusing tissue and producing an enhanced image of the tissue, organs and any differentiation between well-perfused and poorly-perfused tissue, without being injected into the arteries or directly into the area to be imaged. Thus, they may be injected into a peripheral vein or other predetermined area of the body, resulting in considerably less invasion than the arterial injections required for an angiogram. In addition, unlike any of the gaseous bubbles known to the prior art, the metal-containing microparticles of the present invention are quantifiably reproducible. Further, use of microparticles as a contrast agent does not require machinery which is as sophisticated or expensive as that required by radionuclide imaging, nor does their use require exposure to radioactive materials.

Thus, while overcoming many of the problems associated with the prior art, the present invention makes possible the production of unique images of various organ systems. Although the invention technique is applicable to various animal and human body organ systems, its novel features and advantages may be better understood from the following description of its use in obtaining images of myocardial tissue and perfusion or blood flow patterns. The description and accompanying drawings are included for purposes of illustration only, it being expressly understood that they are not intended to be a definition of the limits of the invention.

In reviewing the description and drawings, it should be kept in mind that the heart is a "pump" fed by many blood vessels which, during the course of time, may become partially or totally blocked, causing damage to the heart tissue. In the past, information concerning the state of the blood vessels was primarily obtained through the invasive angiography techniques described above, or through surgery. In addition, information concerning the heart tissue was obtained using radionuclide imaging or surgery; the angiogram produced no direct data regarding the tissue, but rather required the drawing of inferences from data obtained with respect to the major blood vessels and wall motions of the heart.

BRIEF DESCRIPTION OF THE DRAWINGS

The invention will now be described with reference to the accompanying drawings, wherein.

DETAILED DESCRIPTION OF THE INVENTION

Figure 1:
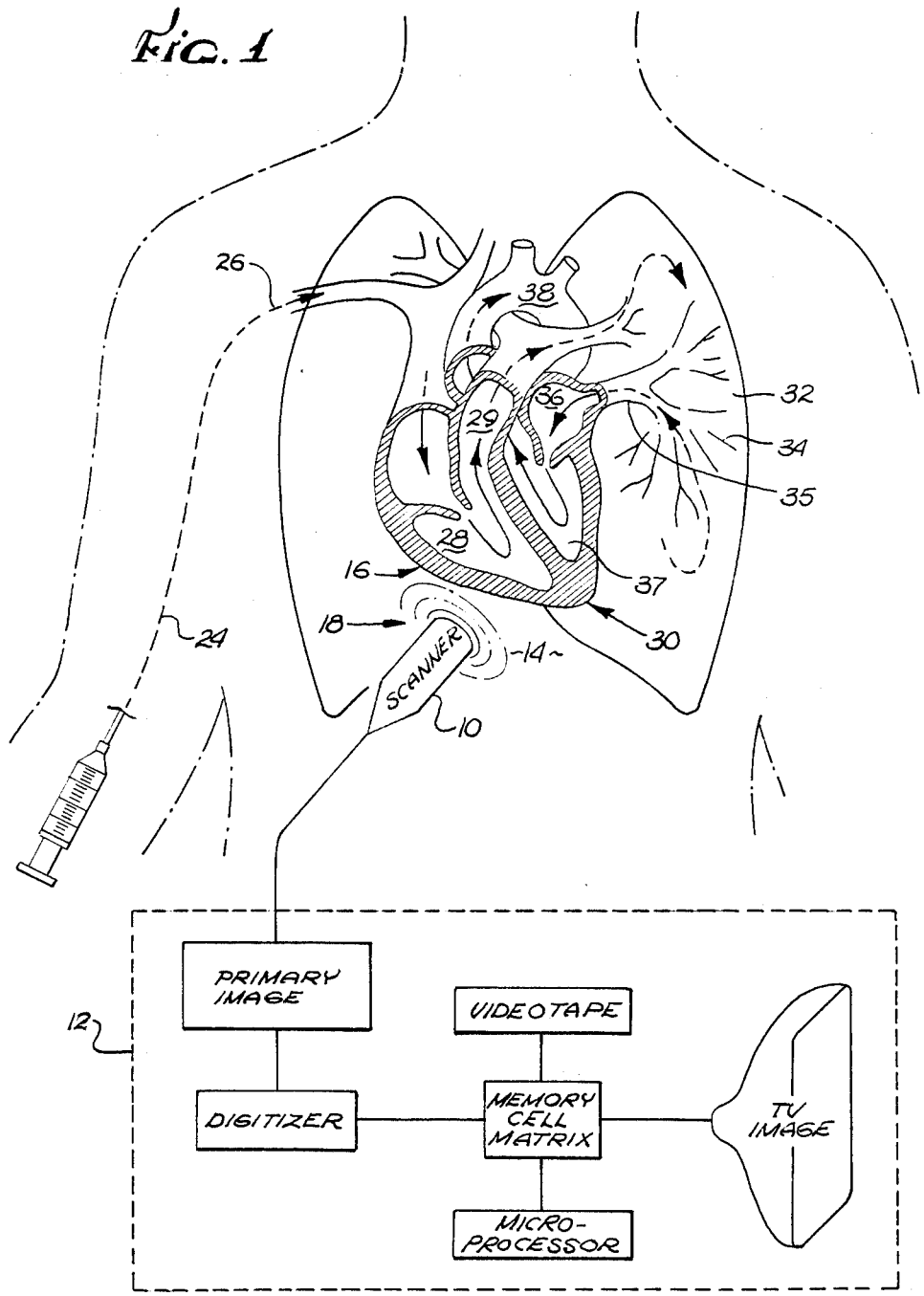
FIG. 1 is a schematic view showing the use of an ultrasonic scanner in echocardiography.

FIG. 1 is a schematic view of the heart and lungs, as well as of ultrasonic scanning equipment consisting of a scanner 10 and imaging apparatus 12. The equipment produces visual images of a predetermined area, in this case, the heart region of a human body. Typically, the scanner 10 is placed directly on the skin 14 over the area to be imaged 16. The scanner 10 houses various electronic components including ultrasonic transducers. The scanner 10 produces ultrasonic waves 18 which perform a sector scan of the heart region 16. The ultrasonic waves 18 are reflected by the various portions of the heart region 16 and are received by the generating transducer and processed in accordance with pulse-echo methods known in the art. After processing, signals are sent to the imaging apparatus 12 (also well known in the art) for viewing.

In the method of the present invention, after the patient is "prepped" and the scanner 10 is in place, the sonicated microbubble or microparticle contrast agent is injected, for example, through an arm vein, generally indicated at 24. The contrast agent flows through the vein 24 in the direction of the arrow 26, through the right (venous) side 28 of the heart 30, through the main pulmonary artery 29 leading to the lungs 32, across the lungs 32, through the capillaries 34, into the pulmonary veins 35 and finally into the left atrium 36 and the left ventricular cavity 37 of the heart 30.

The present invention is directed to both sonicated microbubbles and microparticulate matter used as contrast agents. It has been found that the use of sonicated microbubbles or solid microparticulate matter such as glass or graphite produces images having vividly contrasting areas. In particular, such microparticles (1) are solid or semi-solid, (2) do not contain trapped air, (3) may be biocompatible or biodegradable, (4) are small enough to pass through the capillary beds which are about 8 to 10 microns in size, and (5) have acoustic properties making them echogenic. While not to be bound by any theory, both the sonicated microbubbles and the microparticles of the present invention produce noticeably clearer and more detailed images of the myocardial tissue and microvasculature, as compared with prior art contrast agents.

Referring now to FIGS. 2-5, one can see a contrast echocardiogram produced by the utilization of the sonicated microbubble contrast agent of the present invention. In the figures, a horseshoe-shaped portion 50 represents the left ventricular wall muscle (or tissue) which encloses the left ventricular cavity 37. The microbubbles were injected into the pulmonary artery of a dog and have crossed the capillary beds of the lung to enter the left atrium 36 and the left ventricular cavity 37 into the aorta through the coronary arteries and eventually into the left ventricular tissue 50 enhancing the image thereof.

Figure 2:
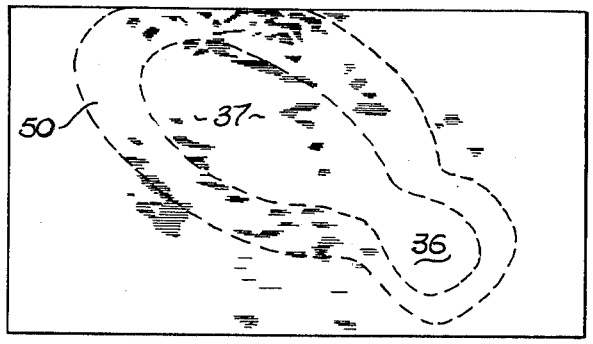
FIGS. 2-5 are cross-sectional images of the heart enhanced by the use of contrast agents flowing therethrough.
Figure 3:
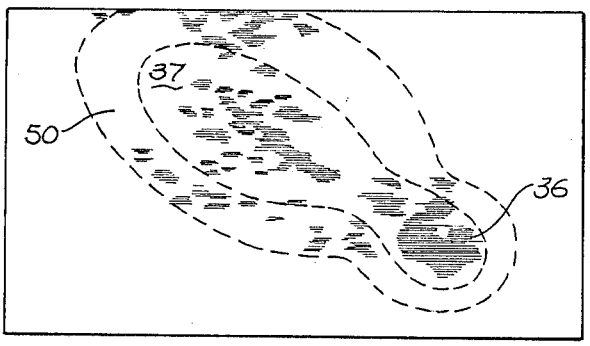
Figure 4:
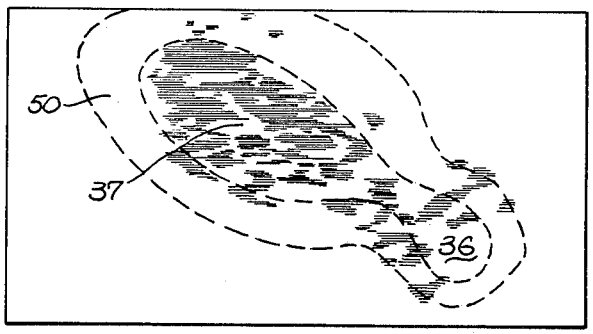
Figure 5:
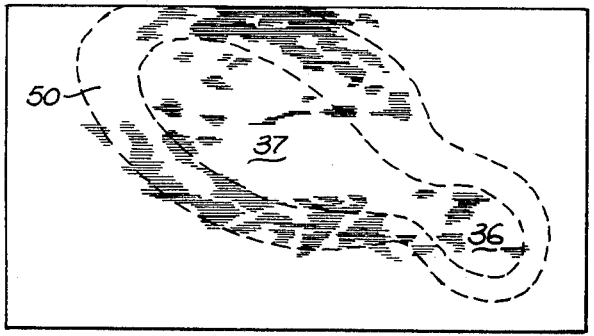

Specifically, FIG. 2 shows a two-dimensional echocardiogram ("2-DE") image of the left ventricular cavity 37 and left atrium 36, prior to the introduction of the sonicated microbubbles. FIG. 3 illustrates the injection of a 10 ml. sonicated Renografin/NaCl mixture through a wedged pulmonary artery catheter. As can be seen, the contrast agent appears in the left atrium 36 and flows into the left ventricle 37. In FIG. 4, substantially complete opacity of the left ventricular cavity 37 has occurred. In FIG. 5, subsequent opacification of the myocardial tissue 50 can be seen. This is because the blood carrying the contrast agent has flowed through the aorta into the coronary arteries which supply the blood to the myocardial tissue 50. Thus, observations and diagnoses can be made with respect to the amount of time required for the blood to pass through the lungs, blood flow patterns, the size of the left atrium, the competence of the mitral valve (which separates the left atrium and left ventricle), chamber dimensions in the left ventricular cavity, and wall motion abnormalities. Upon ejection of the contrast agent from the left ventricle, the competence of the aortic valve also may be analyzed, as well as the ejection fraction or percentage of volume ejected from the left ventricle. Finally, the contrast patterns in the tissue will indicate which areas, if any, are not being adequately perfused.

In summary, such a pattern of images will help diagnose unusual blood flow characteristics within the heart, valvular competence, chamber sizes and wall motion, and will provide a potential indicator of myocardial perfusion.

In the example set forth above, the microbubbles were produced from a mixture of Renografin-76 (a relatively non-toxic, biocompatable radio-opaque dye well known in the art) and saline in a one-to-one ratio. This mixture was sonicated, i.e. subjected to high frequency energy, for about 30 seconds by a Heat System 375 watt sonicator. Such sonicators are well known in the art for other uses, and usually emit ultrasonic energy of 20,000 Hz, although energies of 5,000 to 30,000 Hz or even higher are within the scope of the present invention. Depending on the contrast agent selected, such as the mixture described above, sugar solutions or the like, varying bubble sizes are produced, usually, however, within the desired range of about 6 to 20 microns in diameter.

Besides the scanner 10 briefly described above, there exist other ultrasonic scanners, examples of which are disclosed in U.S. Pat. Nos. 4,143,554 and 4,315,435, the disclosures of which are herein incorporated by reference. Basically, these patents relate to various techniques including dynamic cross-sectional echography (DCE) for producing sequential two-dimensional images of cross-sectional slices of the animal or human anatomy by means of ultrasound energy at a frame rate sufficient to enable dynamic visualization of moving organs. Types of apparatus utilized in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable device in a manner somewhat analogous to radar or sonar displays. While DCE can be used to produce images of many organ systems including the liver, gall bladder, pancreas and kidney, it is frequently used for visualization of tissue and major blood vessels of the heart.

Existing DCE scanners can be classified according to the geometry of their field of view (linear or sector scanning), according to the means used for scanning that field of view (mechanical or electronic scanning) and according to whether the transducer scans the patient or object through an intervening water bath or by direct contact with the surface of the object as, for example, the skin of a patient using an appropriate contact gel or oil. Linear scanners produce a scan of the anatomy consisting of a set of nominally parallel scan lines, displaced with respect to one another by a line spacing roughly comparable to the effective width of each line, as determined primarily by the transducers used in the apparatus. The cross-section imaged by such scanners is therefore approximately rectangular in shape, its width being determined by the line spacing and total number of lines, while its depth is determined by the penetration range of the ultrasound energy into the tissue. Linear scanners are generally used where there is a relatively extended region of the body surface from which access to the parts of interest of the anatomy is possible, such as in the abdominal organs.

Sector scanners produce a scan of the anatomy consisting of a fan of divergent lines spaced angularly from one another, but intersecting (nominally) at a point. The angular spacing is even or uneven, depending upon the apparatus, and is roughly comparable to the effective angular width of each line. Sector scanners are generally used where the anatomical window or region of the body surface from which access to the anatomical part of interest is relatively small, as in the adult heart, the brain and the eye.

Another type of sector scanner is mechanical in nature and can be further divided into two sub-classes, oscillating transducer scanners and rotating transducer scanners. An oscillating transducer scanner is one in which a single transducer is oscillated about an axis nominally lined in the front plane and passing through the center of the transducer with an appropriate angle senso being used to monitor the angular position of the transducer at any time. In a typical rotating transducer scanner, several transducers spin inside a small dome filled with liquid, with one transducer at a time scanning the area of interest. These and other scanners are within the scope of the present invention.

As stated above, in attempting to find a safe, reproducible, quantifiable contrast agent for use in producing an enhanced ultrasonic image of the tissue under study, researchers have used saccharine and gelatin encapsulated microbubbles of nitrogen or carbon dioxide gas having a mean size of approximately 75 microns, pressurized gas in liquids (e.g., $H_2O_2$), and mechanically agitated (hand shaken) mixtures of liquid solutions. However, since the pulmonary artery capillaries are about 8 to 10 microns in diameter, the 75 micron encapsulated microbubbles may not cross the capillary beds and, as a result, their use would require a direct injection into the area to be imaged or an arterial injection involving the same risks as the invasive approach of angiography discussed above. Further, microbubbles produced by agitating various liquids other than by sonicating them) have wide variability of size. Variable amounts of such non-encapsulated agitated microbubbles can pass through capillaries, but the present state of the art has only produced qualitative data due to the inability to control the variables described above. These contrast agents all work to some degree, but suffer from a number of problems including the fact that the size of the bubbles is not uniform. These and other problems are overcome by the sonicated microbubbles of the present invention.

However, while sonicated microbubbles are more uniform in size and produce enhanced images, the potential problems associated with the introduction of air remain. The danger of injecting microbubbles, encapsulated or not, into the heart is that the bubbles eventually collapse and the amount of dissolved air may be toxic in the arterial system (e.g., of the brain and kidneys) as well as in other microcirculatory systems.

Thus, it is evident that the particular contrast agent selected will depend upon the purpose of the imaging. For example, an agent's potential risk factors should be considered for diagnostic or therapeutic uses. The size of the contrast material is also of concern. If the particles are too large they will not pass through the capillaries and thus will require direct or arterial injections if the area to be imaged lies beyond the capillaries. On the other hand, if the contrast agent is too small, it may not reflect sound waves emitted by the ultrasonic transducer.

Solid particulate matter which produces contrast-type enhanced images include graphite particles, glass beads, and similar substances. The present invention has grossly examined many of the available solid particulate matter which theoretically may be used as a contrast agent, and has determined that one such agent, although not previously disclosed as a contrast agent, has a number of very desirable properties. Such agent and associated liquid carriers are broadly disclosed in U.S. Pat. No. 4,247,406 the disclosure which is herein incorporated by reference. In the '406 patent, the solid particulate material comprises magnetically localizable, biodegradable carriers which comprise microspheres formed from an amino acid polymer matrix with magnetic particles embedded therein. For example, albumin can be used as the matrix material and magnetite ($Fe_3O_4$) can be used as the magnetic particles. The microspheres have an average diameter of less than 1.5 microns and the magnetic particles contained therein have an average size of not more than 1,000 Angstroms. The microspheres may contain from 50 to 350 parts by weight of the magnetic material per 100 parts of the amino acid polymer. The microspheres may contain the magnetic particles uniformly distributed throughout the matrix, or, preferably, may be concentrated in the peripheral portions.

Other particles having similar characteristics are also within the scope of the present invention.

By the use of these specifically defined metal-containing solid contrast agents, echocardiograms having the desired resolution may be produced. Further, since the microparticles described above are biodegradable, their side effects are minimized.

The microparticles may be used for imaging a wide variety of areas, even when injected at a peripheral venous site. Those areas include (without limitation): (1) the venous drainage system to the heart; (2) the myocardial tissue and perfusion characteristics during an exercise treadmill test or the like, and (3) myocardial tissue after an oral ingestion or intravenous injection of drugs designed to increase blood flow to the tissue. Additionally, the microparticles may be useful in delineating changes in the myocardial tissue perfusion due to interventions such as: (1) coronary artery vein grafting; (2) coronary artery angioplasty (balloon dilatation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram) an injection of the microparticles may provide data with respect to tissue perfusion characteristics that would augment and complement the data obtained from the angiogram procedure, which identifies only the anatomy of the blood vessels.

Through the use of the microparticles of the present invention, other non-cardiac organ systems including without limitation the liver, spleen, kidney, etc. that are presently imaged by ultrasonic techniques may be susceptible to an enhancement of such currently obtainable images, and/or the generation of new images showing perfusion and flow characteristics that had not previously been susceptible to imaging using prior art ultrasonic imaging techniques.

In terms of method of operation, the use of the subject microparticles would be the same as that described above with respect to sonicated microbubbles. The amount of microparticles used would be dependant on a number of factors including the choice of liquid carriers (water, sugar solution, etc.), degree of opacity desired, areas of the body to be imaged, site of injection and number of injections. In all instances, however, sufficient microparticles would be used in the liquid carrier to achieve discernable images by the use of ultrasonic scanning.

Having described the invention, it is obvious that other modifications may be made by those skilled in the art. For example, other water soluble polymers can be used in place of albumin including hemoglobin, and other magnetic particles can be used in place of magnetite, etc., including magnetic iron oxides, carbonyl iron and the like. This invention, therefore, is to be limited only to the scope and spirit of the appended claims.

What is claimed is:

1. A method of ultrasonic imaging for use in medical procedures, comprising the steps of:
   (a) injecting biodegradable, metal-containing microparticles into a mammal to thereby alter the acoustic properties of a predetermined area; and
   (b) ultrasonically scanning an area including said predetermined area so as to obtain an image of said predetermined area.

2. The method according to claim 1 wherein said microparticles have an average diameter of less than 1.5 microns and are formed from an amino acid polymer matrix with magnetic iron particles embedded therein, said magnetic particles have an average size of not more than 1,000 Angstroms.

3. The method according to claim 1 wherein said predetermined area comprises the heart.

4. The method according to claim 1 wherein said microparticles are injected into the coronary arteries.

5. The method according to claim 1 wherein said microparticles are injected into the peripheral veneous system.

6. The method according to claim 1 wherein, in lieu of said biodegradable microparticles, biocompatable microparticles are used.

7. A method of ultrasonic imaging for use in medical procedures, comprising the steps of:
   (a) subjecting a biocompatible liquid to high frequency energy in the range of about 5,000 to 30,000 Hz so as to produce microbubbles having substantially uniform diameter;
   (b) injecting said microbubbles into a mammal to thereby alter the acoustic properties of a predetermined area; and
   (c) ultrasonically scanning an area including said predetermined area so as to obtain an enhanced image of said predetermined area.

8. The method according to claim 7 wherein said microbubbles have a mean particle size of about 6 to 20 microns.

9. The method according to claim 7 wherein said liquid is subjected to high frequency energy of about 20,000 Hz.

10. The method of claim 7 wherein said biocompatible liquid is a viscous solution.

11. The method of claim 10 wherein said viscous solution is selected from the group consisting of dextrose, sorbitol, relatively nontoxic radio-opaque dye, and mixtures thereof.

12. The method of claim 11 further comprising saline as a diluent.

13. The method of claim 10 wherein said viscous solution is a mixture of relatively non-toxic radio-opaque dye and sodium chloride.

14. The method of claim 7 wherein the step of subjecting said biocompatible liquid to high frequency energy results in cavitation bubbles and said cavitation bubbles collapse resulting in by-product bubbles having substantially uniform diameter.

15. A method of ultrasonic imaging for use in medical procedures, comprising the steps of:
   (a) forming biocompatible microparticles comprising amino acid polymer matrix containing at least one ultrasound image enhancing material selected from the group consisting of air, glass, graphite, nitrogen, carbon dioxide, metal flakes, magnetite, magnetic iron oxides and carbonyl iron;
   (b) injecting said microparticles into a mammal to thereby alter the acoustic properties of a predetermined area; and
   (c) ultrasonically scanning said predetermined area to obtain an ultrasound scanning image thereof.

16. A method of ultrasound imaging for use in medical procedures, comprising the steps of:
   (a) subjecting a biocompatible liquid to high frequency ultrasound energy in the range of about 5,000 to 30,000 Hz thereby producing stable microbubbles having substantially uniform diameters in the range of 6 to 20 microns;
   (b) injecting said microbubbles into a mammal to thereby alter the acoustic properties of a predetermined area thereof; and
   (c) ultrasonically scanning an area including said predetermined area so as to obtain an enhanced image of said predetermined area.

17. A method of ultrasound imaging for use in medical Procedures comprising the steps of:
   (a) providing a biocompatible liquid selected from the group consisting of dextrose, sorbitol, relatively non-toxic radio-opaque dye and mixtures thereof;
   (b) subjecting said biocompatible liquid to ultrasound energy in the range of 5,000 to 30,000 Hz thereby producing stable microbubbles having substantially uniform diameters in the range of 6 to 20 microns;
   (c) injecting said microbubbles into a mammal to thereby alter the acoustic properties of a predetermined area of said mammal; and
   (d) ultrasonically scanning said mammal including said predetermined area thereby obtaining enhanced images of said predetermined area.

18. The method of claim 17 wherein said biocompatible liquid is selected from the group consisting of 70% dextrose, 50% dextrose, 70% sorbitol, a non-toxic radio-opaque dye, and mixtures thereof.

19. The method of claim 17 wherein said biocompatible liquid further comprises saline.

* * * * *